United States Patent
Slazas et al.

(10) Patent No.: US 10,792,173 B2
(45) Date of Patent: *Oct. 6, 2020

(54) STENT DELIVERY SYSTEM AND METHOD

(71) Applicant: DePuy Synthes Products, Inc., Raynham, MA (US)

(72) Inventors: Robert Slazas, Miami, FL (US); Juan A. Lorenzo, Davie, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 151 days.

This patent is subject to a terminal disclaimer.

(21) Appl. No.: 15/939,566

(22) Filed: Mar. 29, 2018

(65) Prior Publication Data

US 2018/0214291 A1    Aug. 2, 2018

Related U.S. Application Data

(63) Continuation of application No. 13/792,466, filed on Mar. 11, 2013, now Pat. No. 9,956,103.

(51) Int. Cl.
*A61F 2/966* (2013.01)
*A61F 2/95* (2013.01)

(52) U.S. Cl.
CPC ...... *A61F 2/966* (2013.01); *A61F 2002/9534* (2013.01); *A61F 2002/9665* (2013.01)

(58) Field of Classification Search
CPC .............. A61F 2/966; A61F 2002/9665; A61F 2002/9534; A61F 2/90; A61F 2/95; A61F 2002/823; A61B 17/12118; A61B 2017/00867; A61B 2017/1205; A61B 2017/2054

USPC .................................................. 623/1.11–1.15
See application file for complete search history.

(56) References Cited

U.S. PATENT DOCUMENTS

| 4,913,141 A | 4/1990 | Hillstead |
| 5,019,085 A | 5/1991 | Hillstead |
| 5,192,297 A | 3/1993 | Hull |
| 5,405,378 A | 4/1995 | Strecker |
| 5,549,122 A | 8/1996 | Detweilwer |

(Continued)

FOREIGN PATENT DOCUMENTS

| JP | H02-189145 A | 7/1990 |
| JP | 4299973 B2 | 7/2009 |

(Continued)

OTHER PUBLICATIONS

European Examination Report for EP App. No. 14158481.3 dated Nov. 6, 2015 (8 pages).

(Continued)

*Primary Examiner* — George J Ulsh
(74) *Attorney, Agent, or Firm* — Mintz Levin Cohn Ferris Glovsky and Popeo, P.C.

(57) ABSTRACT

A system is provided to effectively position a stent within a vessel. The system includes a delivery catheter and a core wire extend through the catheter. The core wire includes an engaging surface region and a capture member disposed thereon, which cooperate to engage a stent such that the stent is able to be advanced or retracted with the advancement or retraction of the core wire. The engaging surface region and the capture member can generally be configured to engage the stent when a portion of the stent is disposed within the lumen of the catheter, and release the stent when no portion of the stent is within the lumen.

13 Claims, 9 Drawing Sheets

(56) References Cited

U.S. PATENT DOCUMENTS

| | | |
|---|---|---|
| 5,596,996 A | 1/1997 | Johanson et al. |
| 5,824,055 A | 10/1998 | Spiridigliozzi et al. |
| 6,110,180 A | 8/2000 | Foreman et al. |
| 6,143,016 A | 11/2000 | Bleam et al. |
| 6,254,612 B1 | 7/2001 | Hieshima |
| 6,468,298 B1 | 10/2002 | Pelton |
| 6,858,034 B1 | 2/2005 | Hijlkema et al. |
| 7,320,703 B2 | 1/2008 | DiMatteo et al. |
| 7,691,109 B2 | 4/2010 | Armstrong |
| 9,956,103 B2 | 5/2018 | Slazas et al. |
| 2001/0056295 A1 | 12/2001 | Solem |
| 2004/0133261 A1 | 7/2004 | Bigus et al. |
| 2005/0043757 A1 | 2/2005 | Arad et al. |
| 2005/0049669 A1 | 3/2005 | Jones et al. |
| 2006/0100531 A1 | 5/2006 | Moser |
| 2006/0259119 A1 | 11/2006 | Rucker |
| 2006/0287644 A1 | 12/2006 | Inganas et al. |
| 2007/0112409 A1 | 5/2007 | Wu et al. |
| 2008/0119943 A1 | 5/2008 | Armstrong et al. |
| 2008/0140178 A1 | 6/2008 | Rasmussen et al. |
| 2008/0300667 A1 | 12/2008 | Hebert et al. |
| 2009/0270974 A1 | 10/2009 | Berez et al. |
| 2010/0114290 A1 | 5/2010 | Rasmussen et al. |
| 2010/0262157 A1 | 10/2010 | Silver et al. |
| 2011/0190862 A1 | 8/2011 | Bashiri et al. |
| 2011/0276121 A1 | 11/2011 | Levine |
| 2012/0059447 A1 | 3/2012 | Zilla et al. |
| 2012/0101562 A1 | 4/2012 | Gunderson et al. |
| 2012/0143304 A1 | 6/2012 | Wübbeling |
| 2014/0257452 A1 | 9/2014 | Slazas et al. |

FOREIGN PATENT DOCUMENTS

| | | |
|---|---|---|
| WO | WO-2007/139689 A2 | 12/2007 |
| WO | WO-2007/139698 A2 | 12/2007 |
| WO | WO-2007/139699 A2 | 12/2007 |
| WO | WO-2008/063156 A2 | 5/2008 |

OTHER PUBLICATIONS

European Search Report for EP App. No. 16203874.9 dated May 10, 2017 (10 pages).

Japanese Office Action for JP App. No. 2014-046179 dated Feb. 6, 2018 (English translation, 4 pages).

STENT DELIVERY SYSTEM AND METHOD

CROSS REFERENCE TO RELATED APPLICATIONS

The present application claims priority to U.S. patent application Ser. No. 13/792,466 entitled "Stent Delivery System and Method" filed Mar. 11, 2013, which is hereby incorporated by reference in its entirety.

FIELD

The present disclosure relates generally to an intravascular implant delivery system and method, and more particularly to a catheter stent delivery system and method.

BACKGROUND

Vascular disorders and defects such as aneurysms and other arteriovenous malformations often occur near the junction of large arteries, for instance at the base of the brain in the Circle of Willis. As aneurysms develop they typically form as a saccular aneurysm protruding from a wall of a vessel and have a neck and a dome portion. Alternatively, aneurysms can form as fusiform malformations that balloon a cross-section of the affected vessel.

Aneurysms and other malformations are especially difficult to treat when located near critical tissue or where ready access to the malformation is not available. Both difficulty factors apply especially to cranial aneurysms. Due to sensitive brain tissue surrounding cranial blood vessels, it is challenging and risky to surgically treat defects of the cranial vasculature.

Alternatives to surgical procedures include endovascular delivery through a catheter delivery device of an intravascular implant, such as an occlusive device in the form of a tubular, self-expanding stent. In one such procedure, an intravascular implant is stored in the distal end of a delivery catheter. The distal end is initially inserted into non-cranial vasculature of a patient, typically a femoral artery in the groin, and guided to the aneurysm. Once the distal end of the catheter is positioned, the stent is advanced, or pushed, distally through the catheter using a pushing surface within the catheter. As the stent is advanced it emerges out of the catheter and self-expands in its current location in the vessel. Such a delivery mechanism is a push-only system; the delivery mechanism pushes the stent out of the catheter, but the stent cannot be moved in the opposite direction within the catheter.

Other mechanisms include dual bumper systems where a stent is radially compressed between two pushing surfaces, one proximal and one distal of the stent. While the entirety of the stent remains within the catheter, the stent can be advanced and retracted in the catheter. However, if the distal portion of the stent is advanced beyond the tip of the catheter, the ability to retract the stent is lost as the diameter of the stent grows to exceed that of the distal most bumper. At this point, the system is a push-only system. Another type of delivery mechanism requires a certain feature to be included on the proximal end of the stent. The delivery mechanism captures the feature on the proximal portion of the stent so that it can be advanced and retracted. Although potentially useful, it is not always feasible or practical to provide such features on a stent.

Accordingly, there remains a need for improved methods and devices that effectively deliver an intravascular implant and allow for a greater degree of manipulation of the intravascular implant.

SUMMARY

A delivery system for conveniently and effectively deploying a stent is provided. The system includes a delivery catheter, such as a microcatheter, a core wire extending through the catheter and having an engaging surface region, and a capture member attached to the core wire. The capture member is able to selectively grasp a stent and maintain it on the core wire between the capture member and the engaging surface of the core wire so that the stent can be advanced or retracted with the advancement or retraction of the core wire. The engaging surface region and the capture member can generally be configured to engage the stent when at least a portion of the stent is disposed within the lumen of the catheter, and release the stent when no portion of the stent is within the lumen.

In some embodiments a stent delivery system includes a delivery catheter having a lumen extending therethrough and an inner diameter. The system further includes a core wire extending through the lumen of the delivery catheter and movable relative to the delivery catheter. The core wire has an outer diameter that is less than the inner diameter of the delivery catheter and an engaging surface region on at least a portion of an outer surface thereof. A capture member is disposed within the delivery catheter and attached to the core wire at a position proximal to the engaging surface region. The capture member has at least one compression member biased to a non-capturing orientation and configured to be oriented in a capturing orientation in alignment with the engaging surface region by a compressive force. The system can also have a selectively deployable stent disposed within the delivery catheter and surrounding the core wire. The stent has an inner diameter that is greater than the outer diameter of the core wire and an outer diameter that is variable between a relaxed state outer diameter and a compressed state outer diameter that is less than the relaxed state outer diameter. The stent is configured such that a proximal portion thereof is secured between the engaging surface region and the capture member and movable relative to the delivery catheter in both a proximal direction and a distal direction when the proximal end of the stent is disposed within the delivery catheter and the stent is released from the engaging surface region and the capture member when the capture member is in the non-capturing orientation.

The engaging surface region of the core wire can be one of a surface feature, an area of higher friction, and an area of lower durometer. In one embodiment the surface feature is selected from the group consisting of teeth, barbs, and pegs. The capture member can include a pair of opposed jaws, wherein the opposed jaws are open in the non-capturing orientation and closed in the capturing orientation. The jaws can be movable to the closed, capturing orientation as a result of being constrained by the inner diameter of the delivery catheter. The jaws can be movable to the open, non-capturing orientation when the jaws are not constrained by the delivery catheter, such as when at least a portion of the jaws extend beyond the distal end of the delivery catheter. The jaws can be movable between the capturing and non-capturing orientations by movement of the core wire relative to the delivery catheter such that the jaws are in the capturing orientation when disposed within the delivery catheter and the jaws are in the non-capturing orientation when the jaws are distal to the a distal end of the delivery catheter. The stent can be advanced beyond a distal end of the delivery catheter, and retracted relative to the delivery catheter when the stent is secured between the engaging surface and the capture member.

In another aspect, a method of deploying a stent includes positioning a stent delivery assembly within a patient, wherein the stent delivery assembly comprises a delivery catheter, a core wire positioned within the delivery catheter and movable with respect thereto, and a radially compressible stent disposed on the core wire and within the delivery catheter. According to the method, the stent is captured within the delivery catheter by a capture member such that the stent is movable proximally and distally while the stent is disposed within the delivery catheter. According to a further aspect of the method, the stent is advanced distally beyond a capture limit of the delivery catheter to free the stent from the capture member and deploy the stent at a desired location within the patient. The capture limit can be the distal end of the delivery catheter.

According to one embodiment, the stent is captured within the delivery catheter by a capture member such that the stent is movable proximally and distally while at least a portion of the stent is not disposed within the delivery catheter and capturing the stent such that an interior surface of the stent is engaged by an engaging surface disposed on the core wire while the stent is held in place on the engaging surface by a compression member.

In another embodiment, a stent delivery device can include a delivery catheter having a lumen extending therethrough and an inner diameter. A core wire extends through the lumen of the delivery catheter and it is movable relative to the delivery catheter. The core wire has an outer diameter that is less than the inner diameter of the delivery catheter and an engaging surface region on at least a portion of an outer surface thereof. A capture member is disposed within the delivery catheter and attached to the core wire at a position proximal to the engaging surface region. The capture member is constrained to a capturing orientation by the delivery catheter such that at least a portion of the capture member is in alignment with the engaging surface region. The capture member is also configured to be in the non-capturing orientation when the capture member is free from constrainment by the delivery catheter. The engaging region of the core wire can include at least one of a surface feature, an area of higher friction, and an area of lower durometer. The surface feature can be selected from the group consisting of a tooth, barb, and peg.

The capture member can include a pair of opposed jaws. The opposed jaws can be open in the non-capturing orientation and closed in the capturing orientation. The jaws can be movable between the capturing and non-capturing orientations by movement of the core wire relative to the delivery catheter such that the jaws are in the capturing orientation when disposed within the delivery catheter and the jaws are in the non-capturing orientation when at least a portion of the jaws is distal to the a distal end of the delivery catheter. The capture member can be advanced beyond a distal end of the delivery catheter, and retracted relative to the delivery catheter when a stent is secured between the engaging surface and the capture member.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

To treat vascular disorders and defects, such as aneurysms and other arteriovenous malformations, intravascular implants, such as stents, can be endovascularly delivered. For instance, a stent can be delivered to the site of a saccular aneurysm and positioned in such a manner as to occlude or block blood pressure and flow to the aneurysm walls. In positioning the stent, it is important to properly place the stent such that flow is blocked to the neck of the aneurysm, while avoiding unnecessary blockage to adjacent vascular tissue.

The present disclosure relates to a delivery system for an intravascular implant, such as a stent. The system utilizes a delivery catheter having a core wire extending therethrough and a stent disposed on and selectively deployable from the core wire. The core wire can be advanced or retracted through the lumen of the catheter and can be effective to guide the catheter from an entry location to the final delivery location within the vasculature, such as from a femoral artery in the leg to the Circle of Willis in the brain. As explained below, features disposed on the core wire enable the stent to be selectively grasped and manipulated such that the stent can be selectively advanced and retracted with the advancement or retraction of the core wire so long as at least a portion of the stent is disposed within the lumen of the catheter. The stent can be released from the core wire when no portion of the stent is within the lumen. By allowing the stent to be both advanced and retracted through the catheter even after a portion of the stent is in an expanded position, the delivery catheter provides an enhanced degree of manipulation and thus facilitates a precise placement of the stent.

Figure 1:
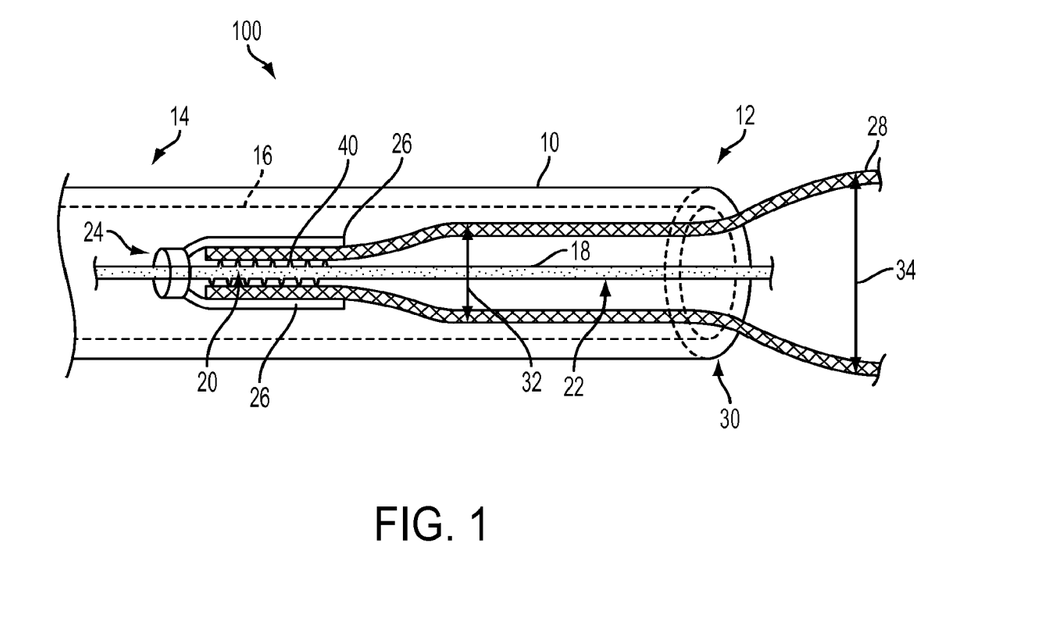
FIG. 1 is a partially transparent schematic view of an exemplary intravascular implant delivery system with a capture member within a catheter lumen.

FIG. 1 illustrates an exemplary embodiment of a stent delivery system 100 that includes a core wire 18, having a engaging surface region 20 and a capture member 24, and a stent 28. The delivery catheter 10 has a distal end 12, a proximal end 14, and a lumen 16 extending therethrough. The core wire 18 extends through the lumen 16 of the delivery catheter 10 and it is movable relative to the delivery catheter 10 such that the core wire 18 is able to be advanced distally through the lumen 16 and retracted proximally through the lumen 16. As noted above, the core wire 18 includes an engaging surface region 20 on at least a portion of the outer surface 22 of the core wire 18 and a capture member 24 attached to the core wire 18 at a position proximal to the engaging surface region 20. The capture member 24 can have at least one compression member 26 biased to a non-capturing orientation and configured to be oriented in a capturing orientation in alignment with a portion of the engaging surface region 20 by a compressive force. When in the capturing orientation, at least a portion of the compression member 26 extends across at least a portion of the engaging surface region 20 so that the compression member 26 effectively lands on the engaging surface region 20.

FIG. 1 illustrates the compression member in the capturing orientation as a result of constrainment by the delivery catheter 10. That is, the delivery catheter 10 constrains the compression member 26 such that it sufficiently overcomes the biasing force to maintain the compression member in the capturing orientation such that it grasps and compresses at least a proximal portion of the stent. In this configuration, the stent 28 is engaged between the compression member 26 and the engaging surface region 20 and thus can be pushed or pulled, i.e., advanced or retracted, through the lumen 16 as needed while at least a portion of the stent remains within the lumen of the delivery catheter 10.

Figure 2:
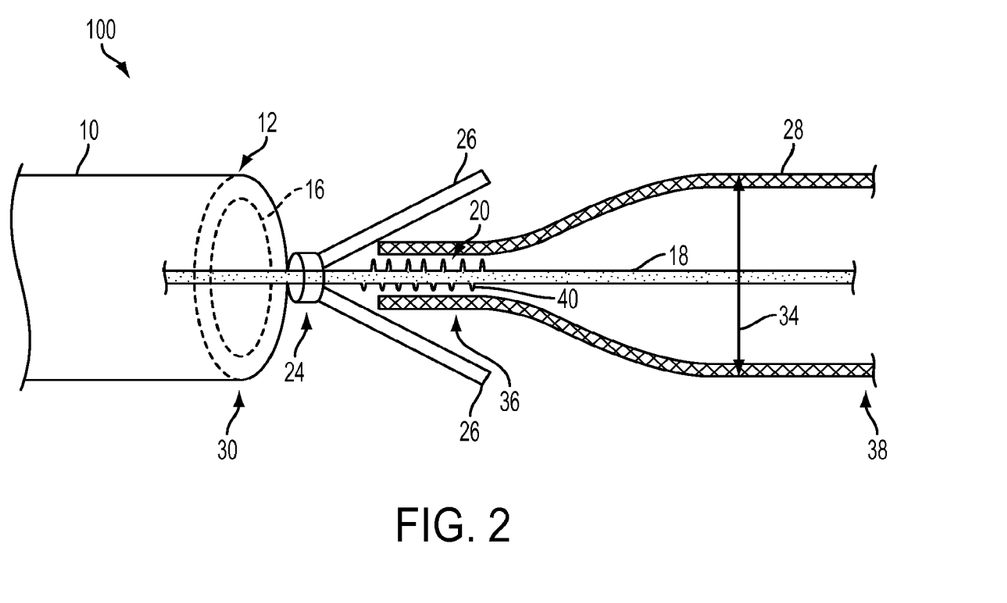
FIG. 2 is a partially transparent schematic view of the intravascular implant delivery system of FIG. 1 with a capture member advanced outside of a catheter lumen.

FIG. 2 illustrates the ability of the system 100 to release the stent 28 as the compression member 26 moves distally, beyond the distal end 12 of the delivery catheter 10, to a non-capturing orientation when the compressive force is removed. That is, when the capture member 24 is not disposed within the lumen 16, the compressive force applied to the compression member 26 by the inner walls of the delivery catheter is absent and the compression member 26 assumes its natural, non-capturing orientation. The stent 28 is thus released and can no longer be manipulated.

The delivery catheter 10 can engage a selectively deployable stent such that the stent 28 remains within the delivery catheter 10 until a desired release point, referred to as the capture limit 30, is met. In some embodiments, the capture limit 30 is the point at which the compressive force is removed from the compression member 26 thus allowing the compression member 26 to move from the capturing orientation to the non-capturing orientation. In one embodiment, as illustrated in FIG. 2, the capture limit 30 coincides with the distal end 12 of the catheter 10.

The delivery device can be configured to manipulate any intravascular implant. In some embodiments, the intravascular implant is a tubular stent 28, such as a self-expanding stent. Exemplary stents can be of any length that is suitable for the intended procedure, and typically are about 10 mm to about 100 mm in length. Self-expanding stents can include stents that are radially compressible such that they have a first, constrained diameter that is smaller than a second, unconstrained diameter that the stent assumes in its natural state. Thus, a self-expanding stent will expand from the first, constrained diameter to the second, unconstrained diameter when the stent is no longer exposed to a compressive force that holds into the constrained diameter.

As shown in FIGS. 1 and 2, the stent 28 can have an inner diameter that is greater than the outer diameter of the core wire 18. For example, the inner diameter can be in the range of about 0.003 inches to about 0.030 inches. The stent 28 can also have an outer diameter that is variable between a relaxed, i.e., unconstrained, state outer diameter 34 and a compressed, i.e., constrained, state outer diameter 32 that is less than the relaxed state outer diameter 34. In some embodiments, the unconstrained diameter 34 is larger than an inner diameter of the delivery catheter 10, and it is sufficiently larger than the inner diameter of a vessel within which the stent 28 is to be placed so as to enable and maintain proper positioning. Generally, vessel diameters will range from about 2 mm to about 5 mm and thus the stent unconstrained outer diameter can be in the range of about 2.5 mm to about 5.5 mm, but the stent can have any desired diameter.

The constrained diameter 32 is sized such that the stent 28 can be disposed on the core wire, for instance by having a clearance fit or a slight interference fit between the outer portion of the engaging surface region 20 and an interior surface of the stent 28. The stent 28 can be configured such that a proximal portion 36 of the stent 28 is secured between the engaging surface region 20 and the capture member 24 and movable relative to the delivery catheter 10 when the proximal portion 36 of the stent is disposed within the delivery catheter 10. By engaging the proximal portion 36 of the stent 28, the stent 28 can be manipulated even when a distal portion 38 is in the unconstrained form as long as at least a portion of the stent is disposed within the delivery catheter. FIG. 2 illustrates a condition in which the stent 28 is released from the engaging surface region 20 and the capture member 24 when the compression member 26 is in the non-capturing orientation thus allowing the proximal portion 36 of the stent 28 to expand from the constrained diameter 32 to the unconstrained diameter 34.

In some embodiments, the delivery catheter 10 is a microcatheter of the type known to those skilled in the art having a lumen 16 extending from the proximal end 14 of the catheter to the distal end 12 of the catheter. An inner diameter of the lumen 16 can be uniform throughout the length of the catheter, or it can vary along the length thereof. For example, the lumen 16 can have an inner diameter in the range of about 0.01 to about 0.05 inches. Exemplary diameters include about 0.016 inches, 0.021 inches, 0.027 inches, 0.035 inches, and 0.044 inches as well dimensions intermediate these values. The outer diameter of the catheter 10 should be sized so as to allow the catheter 10 to advance through a patient's vasculature, for instance by being at least slightly smaller than an inner diameter of any vessel through which it will be passed; for example, less than about 5 mm. Additionally, the catheter 10 should be flexible so as to be maneuverable through the vasculature. The catheter 10 can optionally include a radiopaque portion and a hydrophilic coating to aid in delivery. The catheter can be formed from a variety of suitable materials known to those skilled in the art, including stainless steel, nitinol, platinum, tungsten, polytetrafluorethylene (PTFE), polyamides, polyethers, polyurethanes, silicones, various other polymers and copolymers known to those skilled in the art to have the desired mechanical properties, and braided fiber.

The core wire 18 can be configured to have an intravascular implant disposed thereon and provide for the manipulation of the implant through the lumen 16 of the delivery catheter 10. As explained above, the core wire 18 can be threaded through the lumen 16 of the delivery catheter 10 and extend beyond the distal end 12 of the delivery catheter. For example, a distal portion of the core wire 18 can be threaded through the delivery catheter lumen into the vasculature such that the delivery catheter 10 and any implant therein can be guided to a desired site, such as the site of an aneurysm. Additionally, a proximal end of the core wire 18 can be positioned in such a manner as to allow a user to manipulate the core wire 18, such that the core wire 18 can be advanced in the lumen 16 towards the distal end 12 of the catheter or retracted in the lumen 16 towards a proximal end 14 of the catheter 10. The core wire 18 can also be rotatable relative to the delivery catheter 10. One skilled in the art will appreciate that the core wire should have stiffness properties that render it useful for intravascular delivery techniques. In exemplary embodiments, the core wire 18 has an outer diameter that is less than the inner diameter of the lumen 16. For example, the core wire diameter can be in the range of about 0.003 inches to about 0.020 inches.

As shown in FIGS. 1-7, the engagement surface region 20 of the core wire 18 can take a variety of forms. For example, the engagement surface region 20 can be one of a surface feature 40, an area of lower durometer 42, and an area of higher friction 44. The engagement surface region 20 should be of such dimensions (e.g., length and diameter) such that the stent 28 is able to be held to the core wire with enough force to allow the stent to move with the core wire 18.

Figure 3:
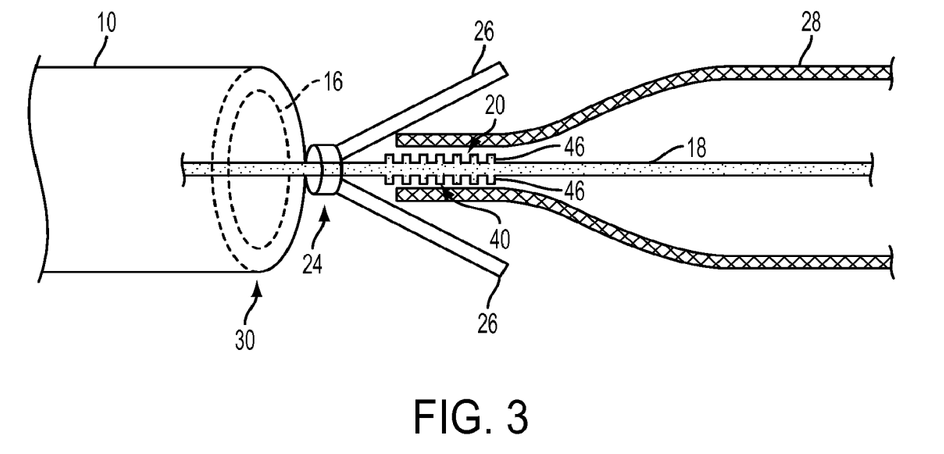
FIG. 3 is a partially transparent schematic view of another exemplary intravascular implant delivery system with a capture member advanced outside of a catheter lumen.
Figure 4:
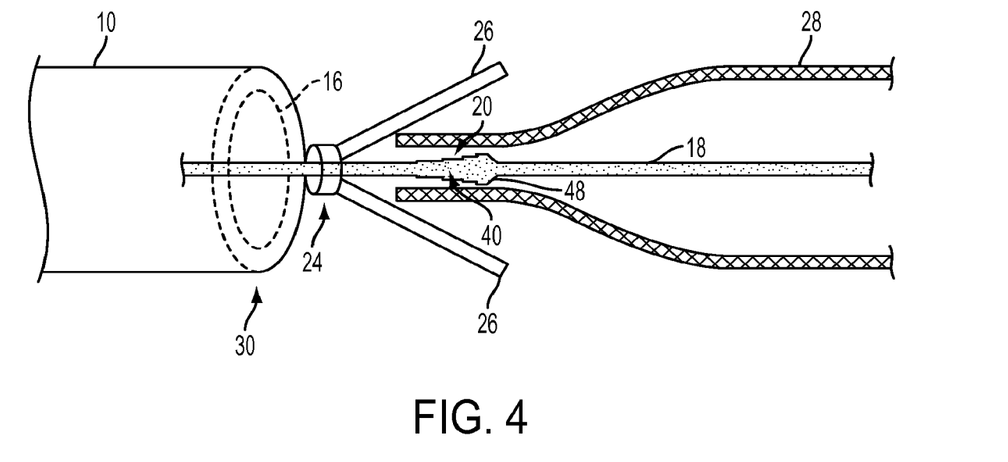
FIG. 4 is a partially transparent schematic view of another exemplary intravascular implant delivery system with a capture member advanced outside of a catheter lumen.
Figure 5:
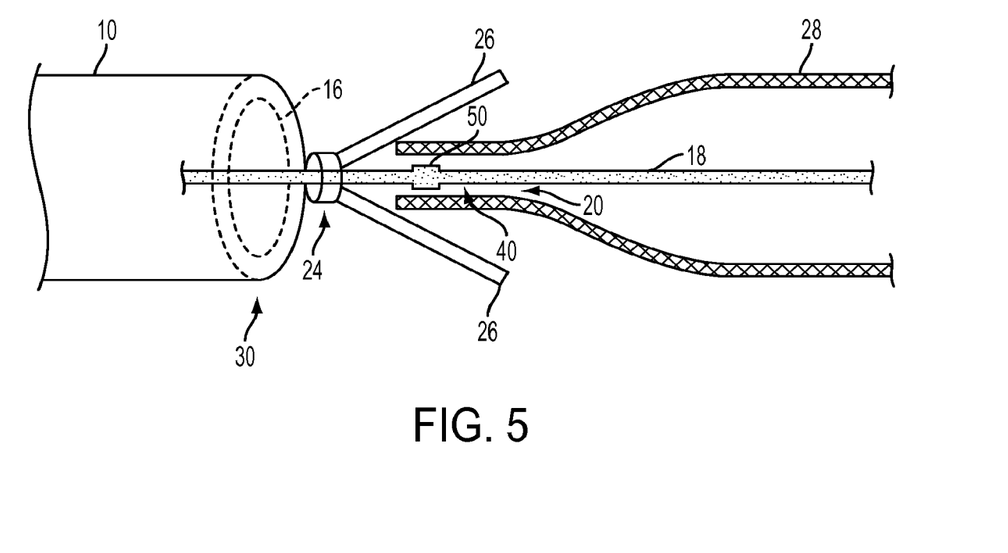
FIG. 5 is a partially transparent schematic view of another exemplary intravascular implant delivery system with a capture member advanced outside of a catheter lumen.

In one embodiment the engagement surface region 20 can include a surface feature 40 configured to retain the stent 28 in place on the engagement surface region 20. The surface feature 40 can include at least one of a teeth 46, barbs 48, or pegs 50. FIGS. 1-2 depict a surface feature that includes a threaded surface feature 40. FIG. 3 shows a surface feature that includes teeth 46. FIG. 4 depicts a barbed surface feature 48. FIG. 5 shows a surface feature having a peg structure 50 extending outwardly from the core wire. The surface feature 40 can be disposed concentrically around the core wire 18, helically around the core wire 18, or can extend from only a portion of the outer surface of the core wire 18.

As mentioned above, the surface feature 40 should be of such dimensions that the stent 28 is able to be held to the core wire 18, with the assistance of the capture member 24, with enough force to allow the stent 28 to move with the core wire 18. The surface feature 40 should be small enough to allow the stent 28 to be released from the engaging surface region 20 when the stent 28 is in the unconstrained orientation and should be smaller than the inner diameter of the lumen 16 so as to allow movement therethrough, for example the surface feature 40 can have an outer diameter in the range of about 0.003 inches to about 0.05 inches. The surface feature can extend along the core wire 18 distally from the capture member 24 so as to have enough surface area to effectively engage the stent 28. The surface feature 40 can be disposed on only a portion of the length of the engagement surface region 20 or the surface feature 40 can be disposed along the entire length of the engagement surface region 20. For example, the surface feature 40 can have a length in the range of about 1 mm to about 10 mm.

Figure 6:
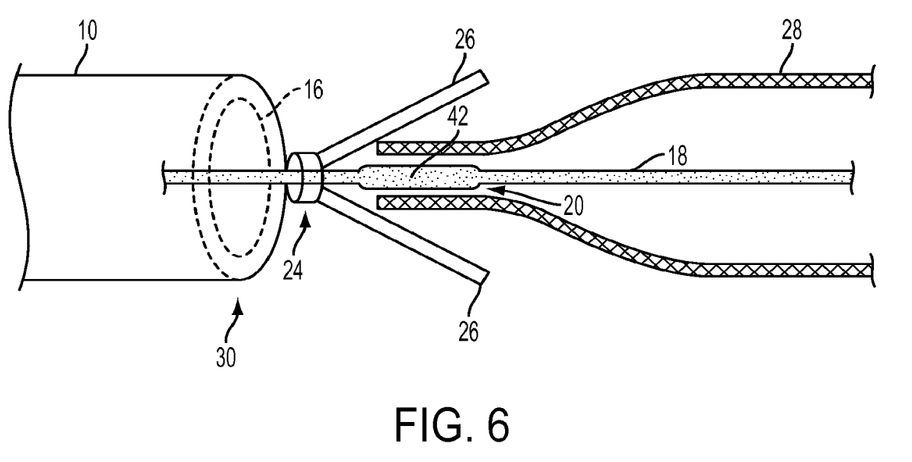
FIG. 6 is a partially transparent schematic view of another exemplary intravascular implant delivery system with a capture member advanced outside of a catheter lumen.

In other embodiments the engagement surface region 20 can include an area of lower durometer 42, such as a low-durometer polymer. The area of lower durometer 42 can be disposed directly on the core wire such that the outer diameter of the core wire is substantially the same in the area of lower durometer 42 as on the rest of the core wire, or, the area of lower durometer 42 can be disposed on the core wire such that the diameter of the engagement surface region 20 is greater than that of the core wire, as shown in FIG. 6. In some embodiments the low durometer area 42 can have a hardness range of about 40 Shore D to about 10 Shore A. For example, a silicone coating may be applied to a portion of the core wire to form the engaging surface. Other low-durometer polymers can include polyurethane elastomers, polyamides, polyethers, silicones, nitriles, and synthetic and natural rubbers. As mentioned above, the area of lower durometer 42 should be of such dimensions that the stent 28 is able to be held to the core wire 18, with the assistance of the capture member 24, with enough force to allow the stent 28 to move with the core wire 18. The diameter of the area of lower durometer 42 should be small enough to allow the stent 28 to be released from the engaging surface region 20 when the stent 28 is in the unconstrained orientation and should be smaller than the inner diameter of the lumen 16 so as to allow movement therethrough, for example the area of lower durometer 42 can have an outer diameter in the range of about 0.003 inches to about 0.05 inches. The area of lower durometer 42 can extend along the core wire 18 distally from the capture member 24 so as to have enough surface area to effectively engage the stent 28. The area of lower durometer can include the entire surface area of the engagement surface region 20 or it can be disposed on only a portion thereof. For example, the area of lower durometer can have a length in the range of about 1 mm to about 10 mm.

Figure 7:
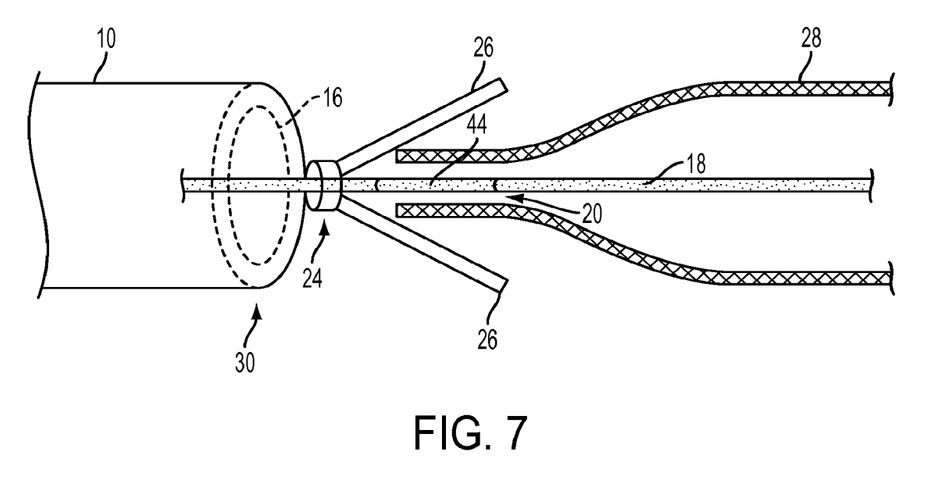
FIG. 7 is a partially transparent schematic view of another exemplary intravascular implant delivery system with a capture member advanced outside of a catheter lumen.

In yet another embodiment, as shown in FIG. 7, the engagement surface region can be an area of higher friction 44. The area of higher friction 44 can be formed of textured metal, such as ribbing, cross-hatching, stippling, dimpling, or any other feature that is more rough than the remainder of the core wire. The area of higher friction can alternatively be in the form of a coating that provides a high-friction surface, similar to that as described above in relation to the area of lower durometer 42. For instance, high-friction microfibers, tungsten alloy coatings, and other metallic and polymeric coatings can be disposed on the engaging surface region to provide high friction between the engaging surface region and the stent. As mentioned above, the area of higher friction 44 should be of such dimensions that the stent 28 is able to be held to the core wire 18, with the assistance of the capture member 24, with enough force to allow the stent 28 to move with the core wire 18. The diameter of the area of higher friction 44 should be small enough to allow the stent 28 to be released from the engaging surface region 20 when the stent 28 is in the unconstrained orientation and should be smaller than the inner diameter of the lumen 16 so as to allow movement therethrough, for example the area of higher friction 44 can have an outer diameter in the range of about 0.003 inches to about 0.05 inches. The area of higher friction 44 can extend along the core wire 18 distally from the capture member 24 so as to have enough surface area to effectively engage the stent 28. The area of higher friction 44 can include the entire surface area of the engagement surface region 20 or it can be disposed only on a portion thereof. For example, the area of higher friction 44 can have a length in the range of about 1 mm to about 10 mm.

As noted above, the capture member 24 can include at least one compression member 26. In some embodiments, the compression member 26 includes one or more jaw members 26. The jaws 26 are arranged as radial levers hinged in the same axial location on the core wire 18, which are formed so as to be biased in a non-capturing orientation. The non-capturing orientation refers to an open position where an angle formed between the core wire 18 and the jaw member 26 is large enough that the stent is not contacted by the jaw member 26 and thus the stent is allowed to assume the relaxed, unconstrained diameter 34. When there are multiple jaws, they can be disposed adjacent one another about the core wire 18 such that the jaws 26 oppose one another. The capture member 24 is configured to fill the space between the stent 28 and the inner wall of the lumen 16 such that the stent 26 is held in place between the capture member and the engaging surface 20 while maintaining sufficient clearance to allow the stent 28 to be manipulated through the lumen 16, i.e., moved proximally and distally within the lumen of catheter 10. An exemplary jaw member 26 has a length that is large enough to provide adequate force to keep the stent 28 in place when in the captured position, but small enough to not substantially affect the flexibility of the catheter 10. For example, the jaw or compression member 26 can be in the range of about 1 mm to about 10 mm in length.

As an alternative to the jaws described above, one skilled in the art will appreciate that the capture member 24 can be formed of any member effective to compress the stent 28 to the engaging surface region 20. For example a collet-type member, collar, clamp, or spring structure can be used. The capture member 24 can be formed of any suitable material, as one skilled in the art will appreciate, such as stainless steel, nitinol, platinum, tungsten, polytetrafluorethylene (PTFE), polyvinyl chloride, and other metallic and polymeric materials.

Figure 8:
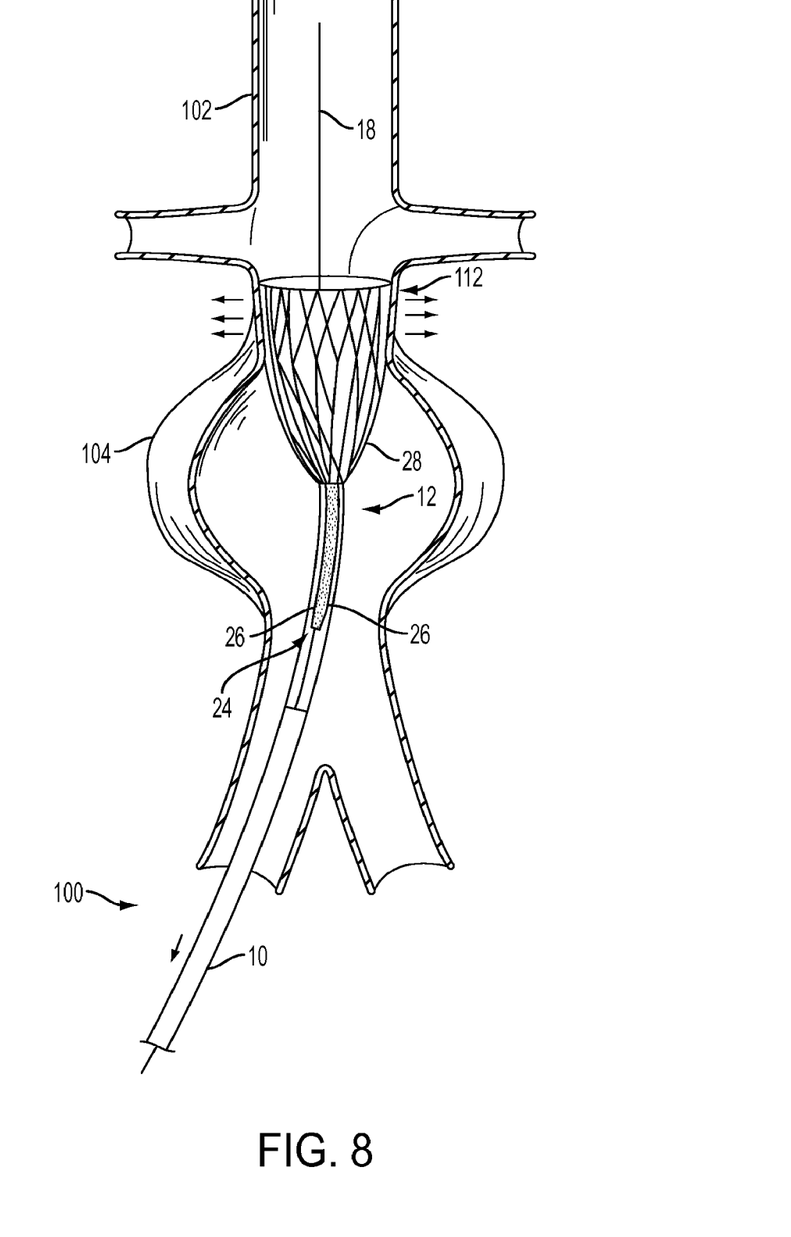
FIG. 8 is a schematic view of an exemplary intravascular implant delivery system according to the present invention illustrating the delivery of a stent within a vessel.

FIG. 8 illustrates the use of system 100 for delivering a stent 28 to a blood vessel 102 having an aneurysm 104. As shown, a proximal end of stent 28 is grasped by the jaws of a compression capture member 26 in a capturing orientation such that the stent 28 is able to be manipulated within the vessel 102 and the catheter 10. The distal end 12 of the catheter is placed near a distal end of a target aneurysm 104 such that a distal portion 112 of the stent 28 is in proximity to the vessel 102 in its unconstrained form. Once the distal end 12 of the catheter is in the general area desired for placement, a user can manipulate the stent 28 by advancing and retracting the stent 28 within the catheter 10, and optionally advancing and retracting the catheter 10 as well, to achieve the optimal positioning of the distal portion 112 of the stent 28. The catheter 10 is then moved to the opposite side of the aneurysm 104, advancing and retracting the stent 28 as necessary to ensure proper placement is maintained. As the stent 28 exits the distal end 12 of the catheter, the stent 28 expands to its unconstrained diameter, but as long as a proximal portion of the stent 28 is engaged by the capture member 24, the stent 28 can be retracted back into the catheter 10.

Figure 9:
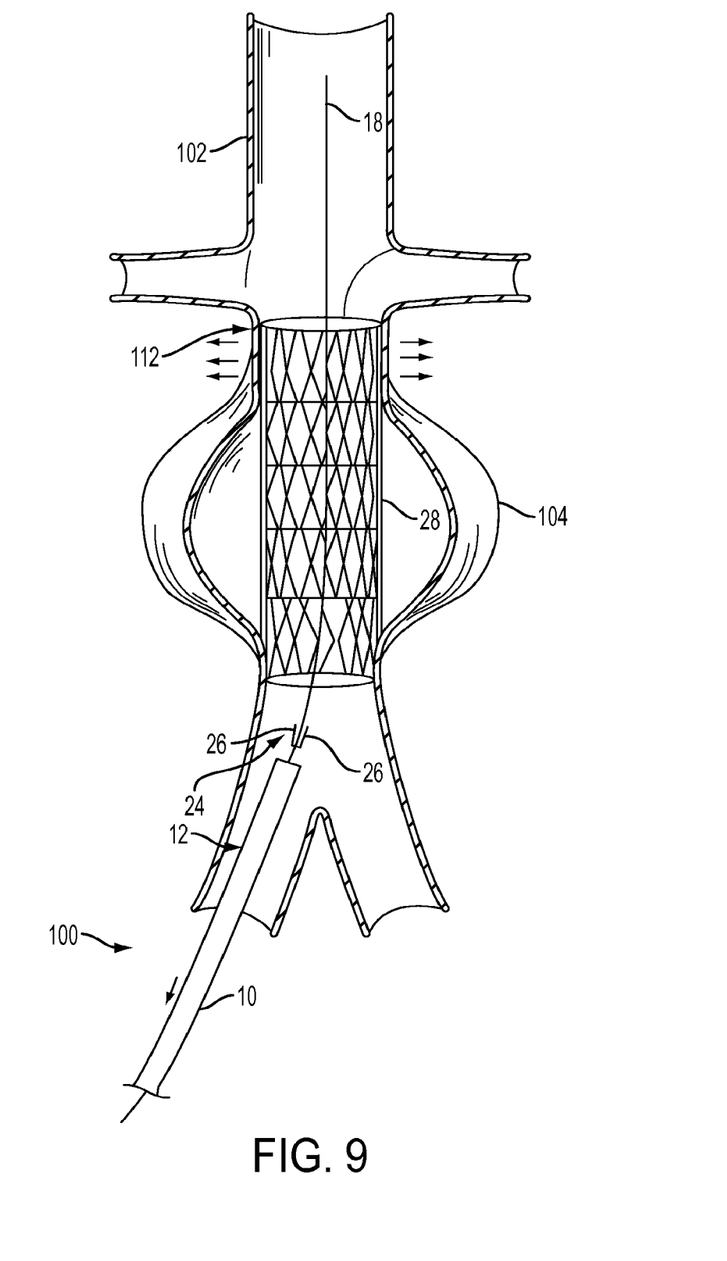
FIG. 9 is a schematic view of an exemplary intravascular implant delivery system according to the present invention following the delivering of a stent within a vessel.

FIG. 9 shows the stent 28 fully positioned within the vessel 102 to treat the aneurysm 104. As so positioned the stent 28 is able to limit blood flow to the aneurysm 104 by spanning the length of the aneurysm 104. As shown, once the stent 28 is positioned as desired, the capture member 24 is advanced beyond the distal end of the catheter 10 to allow the capture member 24 to assume its non-capturing orientation. When in the non-capturing orientation, the proximal portion of stent 28 is no longer engaged between the engaging surface region 20 and the capture member 24 and the the proximal portion of the stent assumes its unconstrained diameter. Once the stent 28 is placed in its desired position and is released from the capture member 24, the delivery catheter 10 can be removed from the vasculature.

A person skilled in the art will appreciate that the present invention has application in conventional minimally-invasive and open surgical instrumentation as well application in robotic-assisted surgery. While in many cases the description uses cranial vasculature, aneurysms, and stents configured for the treatment thereof as an exemplary delivery location and implant, this is by way of illustration only. The methods and devices described herein can be applied to virtually any vasculature, defect, and intravascular implant.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A stent delivery system, comprising:
   a catheter including a lumen extending therethrough;
   a stent disposed within the lumen of the catheter, the stent including a lumen extending therethrough;
   a core wire disposed within the lumen of the stent; and
   a capture member having a proximal end attached at a fixed position to the core wire, and the capture member being disposed entirely within the lumen of the catheter, being biased radially outward, and grasping a proximal portion of the stent within the lumen of the catheter and thereby pressing the proximal portion of the stent radially inward toward the core wire;

wherein the stent, the core wire, and the capture member are configured to be collectively moved proximally and distally within the lumen of the catheter with the capture member pressing the proximal portion of the stent radially inward toward the core wire; and wherein, with the capture member pressing the proximal portion of the stent radially inward toward the core wire, a distal end of the stent is freely expandable radially outward relative to the core wire and the capture member and configured to automatically expand radially outward outside of the lumen of the catheter in response to the distal end of the stent advancing distally out of a distal opening of the lumen of the catheter.

2. The system of claim 1, wherein a roughened area extends along a partial longitudinal length of an outer surface of the core wire, and the capture member is pressing the stent radially inward against the roughened area.

3. The system of claim 1, wherein an area having a first durometer extends along a partial longitudinal length of an outer surface of the core wire, the first durometer is less than a durometer of a remainder of the outer surface of the core wire, and the capture member is pressing the stent radially inward against the area having the first durometer.

4. The system of claim 1, wherein an outer surface of the core wire includes one of a plurality of barbs extending radially outward therefrom, a plurality of pegs extending radially outward therefrom, and a plurality of teeth extending radially outward therefrom, and the capture member is pressing the stent radially inward against the one of the plurality of barbs, plurality of pegs, and plurality of teeth.

5. The system of claim 1, wherein, with the stent disposed within the lumen of the catheter, the distal end of the stent is freely expandable radially outward relative to the core wire and the capture member.

6. The system of claim 1, wherein the capture member includes a jaw biased radially outward.

7. The system of claim 1, wherein the capture member includes one of a collet-type member, a collar, a clamp, and a spring structure, the one of the collet-type member, the collar, the clamp, and the spring structure being biased radially outward.

8. A stent delivery system, comprising:
a catheter including a lumen extending therethrough;
a stent disposed within the lumen of the catheter, the stent including a lumen extending therethrough;
a core wire disposed within the lumen of the stent; and
a capture member having a proximal end attached at a fixed position to the core wire, and the capture member being disposed entirely within the lumen of the catheter, being biased radially outward, and grasping a proximal portion of the stent within the lumen of the catheter and thereby pressing the proximal portion of the stent radially inward toward the core wire;

wherein the stent, the core wire, and the capture member are configured to be collectively moved proximally and distally within the lumen of the catheter with the capture member pressing the proximal portion of the stent radially inward toward the core wire;

wherein, with the capture member pressing the proximal portion of the stent radially inward toward the core wire, a distal portion of the stent is configured to automatically expand radially outward outside of the lumen of the catheter in response to the distal portion of the stent advancing distally out of a distal opening of the lumen of the catheter; and wherein, with the stent disposed within the lumen of the catheter and with the capture member pressing the proximal portion of the stent radially inward toward the core wire, a distal end of the stent is freely expandable radially outward relative to the core wire and the capture member.

9. The system of claim 8, wherein a roughened area extends along a partial longitudinal length of an outer surface of the core wire, and the capture member is pressing the stent radially inward against the roughened area.

10. The system of claim 8, wherein an area having a first durometer extends along a partial longitudinal length of an outer surface of the core wire, the first durometer is less than a durometer of a remainder of the outer surface of the core wire, and the capture member is pressing the stent radially inward against the area having the first durometer.

11. The system of claim 8, wherein an outer surface of the core wire includes one of a plurality of barbs extending radially outward therefrom, a plurality of pegs extending radially outward therefrom, and a plurality of teeth extending radially outward therefrom, and the capture member is pressing the stent radially inward against the one of the plurality of barbs, plurality of pegs, and plurality of teeth.

12. The system of claim 8, wherein the capture member includes a jaw biased radially outward.

13. The system of claim 8, wherein the capture member includes one of a collet-type member, a collar, a clamp, and a spring structure, the one of the collet-type member, the collar, the clamp, and the spring structure being biased radially outward.

* * * * *